United States Patent [19]
Makower et al.

[11] Patent Number: 5,613,966
[45] Date of Patent: Mar. 25, 1997

[54] SYSTEM AND METHOD FOR ACCESSORY RATE CONTROL

[75] Inventors: Joshua Makower, New York, N.Y.; David A. Zieve, Louisville, Colo.; Frank Barber, Brattleboro, Vt.

[73] Assignee: Valleylab Inc, Boulder, Colo.

[21] Appl. No.: 360,534

[22] Filed: Dec. 21, 1994

[51] Int. Cl.$^6$ .................................................. A61B 17/36
[52] U.S. Cl. .................. 606/34; 606/41; 606/10; 604/30
[58] Field of Search ........................... 606/10–12, 32–34, 606/37–42, 45–50; 604/21, 22, 30, 35

[56] References Cited

U.S. PATENT DOCUMENTS

| | | |
|---|---|---|
| 4,209,018 | 6/1980 | Meinke et al. . |
| 5,108,389 | 4/1992 | Cosmescu . |
| 5,152,762 | 10/1992 | McElhenney . |
| 5,160,334 | 11/1992 | Billings et al. . |
| 5,324,283 | 6/1994 | Heckele . |

*Primary Examiner*—Angela D. Sykes
*Assistant Examiner*—Michael Peffley
*Attorney, Agent, or Firm*—Peter C. Richardson; Lawrence C. Akers; Aaron Passman

[57] ABSTRACT

A system changes the rate of operation of a smoke evacuator used with an electrosurgical generator during treatment of a patient electrosurgically at an operative site. A mono or bipolar circuit for electrosurgery has an electrosurgical generator, ESU. A switch in the circuit activates the ESU when keyed. An active output connects the ESU to supply radio frequency energy and a return input to the ESU receives energy. A handpiece has an active electrode and an active lead connects between the output and the electrode. A return lead connects the return input and has a terminus to the patient. A controller in the ESU controls the various output signals of the ESU in response to hand or foot switching inputs or sensed current in the patient circuit. A trigger is connected to the controller in the ESU. The smoke evacuator operates at a different rate when the trigger in the ESU is keyed. A rate controller adjusts the condition of its function per unit time in accord with the trigger on the ESU. Terminals on the ESU deliver signals from the trigger through connections between the terminals and the smoke evacuator. Also a smoke detector near the electrode can find smoke thereabout and delivers a signal during operation of the ESU. The smoke evacuator senses the signal and changes the rate controller from a low level of fluid flow through therethrough to a high flow for drawing fluid from the area about the active electrode. The rate controller adjusts. The switch is located on the handpiece or a foot pedal. A method for changing the rate of operation of a smoke evacuator has steps including having a circuit for electrosurgery associated with the ESU. Connecting a switch activates the ESU. The rate of the smoke evacuator is adjusted with the keying of the ESU or with sensed current from the patient circuit.

17 Claims, 2 Drawing Sheets

SYSTEM AND METHOD FOR ACCESSORY RATE CONTROL

BACKGROUND OF THE INVENTION

This invention relates to a system for rate control of an accessory used when an electrosurgical generator is keyed. More specifically, the system is coupled with terminals of the electrosurgical generator for receiving signals when RF energy is produced by the generator and then changing the rate at which the accessory is operated.

BACKGROUND OF THE DISCLOSURE

Accessories or simultaneous subsystems are frequently used concurrently with or at the same time as electrosurgical generators particularly with laparoscopic procedures. Operation of those accessories with the same controls as used to operate the electrosurgical generator is often desirable. Hand and foot operated switches are typically connected into the generator with terminals and replaceable connectors on the wiring to the hand or foot switch.

U.S. Pat. No. 5,324,283 has a switch on a medical instrument for accessory devices used for example, in endoscopic surgery. A control section is light transmitting and extends between a light source and a light receiver and partly through the instrument. The output of the light receiver controls the external accessory devices operation. The light beam, arriving at light receiver along the light transmitting control section, is altered by the switch so that the external device can be turned on and off.

U.S. Pat. No. 5,160,334 has an electrosurgical generator and suction apparatus in which a switching circuit connected to a hand switch or foot switch operates the electrosurgical generator from a remote location, i.e. the surgeon's hand or foot. The switching circuit activates a controller for a vacuum motor plumbed to remove the smoke that results at the site of the electrosurgery. It is clear that the remote operation of the switching circuit for the smoke evacuator by the hand or foot switch must be hard wired, i.e. pass through internal wires in the electrosurgical unit. This approach is a disadvantage to the many of existing electrosurgical generators presently in operation in hospitals throughout the world since the internal wiring for automatic activation of the accessory is required in the electrosurgical generator for the automatic activation of the suction apparatus. It is desired to be able to have an automatic activation for any accessory that can be easily used to facilitate the start of the accessory. Operation of accessories such as a smoke evacuator or insufflation system, a light or video system, a monitoring system, or other similar apparatus used in conjunction with and during electrosurgery is frequently needed during surgery.

U.S. Pat. No. 4,209,018 has a tissue coagulation apparatus and wherein indicating means is in circuit with the active and return electrode leads such that an output signal from the indicating means provides information to a control for the electrosurgical generator. The specific indicating means can respond to various physical values showing the presence and strength of an electrical arc between the distal ends of bipolar electrodes. The purpose of the device of this patent is to control the strength of the arc whereby the heat applied during electrosurgery is closely controlled to minimize or avoid tissue cell rupture and/or burning of albumin. Control of the arc is designed to minimize the effects of changing tissue which could cause over heating of the tissue cells resulting in steam explosions and uncontrolled cutting or coagulating. The monitoring function provided by the indicating means is used to control internal circuitry within the electrosurgical generator by means of the control wired directly to the generator, There is no teaching of the indicating means controlling something external of the generator such as the an accessory. The electrically connected (hard wired) indicating means is merely an external pick-up for the control and does not have an external output for an accessory.

Any number of internal inductive pick-ups have been proposed and used for control of RF leakage. U.S. Pat. No. 5,152,762 discloses an inductive pick-up and references prior patents which use a winding on a common magnetic core about which the active and return leads are also wound. When there is an unbalanced between the flow of current through the active and return leads an EMF is generated in the extra winding, that EMF is used as a signal to control the RF leakage and maintain the balance the flow of energy in the active and return leads. Inductive coils for leakage are internal with respect to the electrosurgical generator and as such precede the output connections on the exterior of the generator. They are sensitive to inductive differences in the active and return leads, but provide no external signal for use with an accessory.

U.S. Pat. No. 5,108,389 discloses an automatic activation system for a smoke evacuator used with a laser. A foot switch is arranged to break a laser beam as a signal to operate the smoke evacuator. There is no physical association or external electrical coupling or attachment between the laser and the smoke evacuator. That is to say that, when the laser beam is transmitted and received, the foot switch interrupts the laser beam and thus provides a signal. A receiver mounted to the foot switch and associated therewith signals laser operation. That apparatus, as disclosed, is nothing more than a switch that makes an electrical connection when an optical signal is interrupted.

The references noted herein are incorporated by reference and made a part of this disclosure.

SUMMARY OF THE INVENTION

A system changes the rate of operation of an accessory used with an electrosurgical generator during treatment of a patient electrosurgically at an operative site. An electrosurgical circuit is preferably used in electrosurgery and is between the electrosurgical generator and the patient. A hand operated or foot operated switch may permit activation of the electrosurgical generator controller when keyed during treatment of the patient. A return input in the circuit and electrically connected to the electrosurgical generator most preferably receives electrosurgical energy in the circuit with the patient. An electrosurgical handpiece is any active instrument such as an electrosurgical pencil, an endoscopic tool of any configuration or the like in the circuit and may have at least an active electrode carried thereby for use in providing electrosurgical procedures. Electrosurgical handpiece will be used throughout this disclosure and its claims to cover any and all such instruments. An active lead may be connected in the circuit between the active output and the electrosurgical handpiece active electrode. A return lead most preferably connects in the circuit and to the return input and may have a return positioned relative to the patient for completing the circuit with the active electrode so that RF energy passing therethrough may be returned to the electrosurgical generator through the return input.

A trigger is connected to the controller in the electrosurgical generator. The controller may receive signals indicating output current flow. The trigger may be activated when the handswitch or footswitch is keyed or it may be activated by the controller in response to the electrosurgical current flow or some combination of input signals. An accessory may preferably be operated at a different rate when enabled by the trigger in the electrosurgical generator.

A rate controller in the accessory may adjust the condition of its function per unit time in accord with instructions from the trigger. Specifically, the trigger signals from the electrosurgical generator. One or more terminals on the electrosurgical generator might deliver one or more signals indicative of the trigger operation. Keying the electrosurgical generator on can provide one signal and keying the electrosurgical generator off can provide another signal. Connections are preferably between the terminals and the accessory.

The system for an accessory may be a smoke evacuator and/or insufflator for drawing fluid through a passage near the electrosurgical handpiece active electrode; the passage maybe associated with the handpiece or included in or on the handpiece. The rate controller preferably changes the smoke evacuator from a low level of fluid flow through the passage from the active electrode to a high flow for drawing fluid from the area about the active electrode. The rate controller may be adjustable so that the low level of fluid flow is that required to barely purge fluid through the passage from the active electrode and the high flow rate is able to remove fluid in the vicinity of the active electrode.

The electrosurgical circuit might be in one embodiment monopolar wherein the return includes a return pad connected to the patient and the return lead. The electrosurgical circuit may be in another embodiment bipolar wherein the return may include a second electrode carried on the handpiece. The two electrodes are preferably, in the bipolar arrangement, mounted adjacent to one another. The second electrode connects to the return lead and the second electrode is operatively associated with the first electrode attached to the active lead for electrosurgical effects between the two electrodes.

The terminals in one configuration may be on the electrosurgical generator and are associated physically with and electrically coupled to the trigger to provide signals when the electrosurgical generator is keyed.

The switch is preferably located on the handpiece for the keying of the electrosurgical generator. The switch may be alternately located on a pedal for foot operation and the switch connects to the electrosurgical generator for the keying of the electrosurgical generator. A video monitor may be connected to the terminals for receiving the signals to provide sound and/or image blanking when the electrosurgical generator is keyed. If the audio is controlled, the volume may be raised or lowered during electrosurgery.

The accessory may be a light for the operative site and the rate controller may include a light intensity varying means for changing the intensity from a low level using minimal power to a high level for optimum observation and illumination.

A method for changing the rate of operation of an accessory used with an electrosurgical generator during treatment of a patient electrosurgically at an operative site has steps including having a circuit for electrosurgery wherein the circuit may be associated with the electrosurgical generator and the patient. Another step is connecting a switch in the circuit to activate the electrosurgical generator when keyed during treatment of the patient. It is preferred to supply radio frequency energy for the patient to an active output in the circuit with the active output electrically connected to the electrosurgical generator. Then the step, of receiving electrosurgical energy in the circuit from the patient with a return input in the circuit wherein the return input electrically connects to the electrosurgical generator, may be followed. An added step may be providing an electrosurgical handpiece in the circuit and the electrosurgical handpiece having at least an active electrode carried thereby for use in performing electrosurgical procedures. Connecting active and return leads in the circuit between the respective active output and return input is one more step. The further step of connecting the return lead in the circuit and to the return input is performed. Then the step, of having the return positioned relative to the patient for completing the circuit with the active electrode for returning RF energy passing therethrough to the electrosurgical generator through the return input, may be used. Operating an accessory at a different rate when the electrosurgical generator is keyed is a further step in the method. Adjusting the accessory for the condition of its function per unit time in accord with the keying of the electrosurgical generator with a rate controller is another step. Delivering a signal indicative of the use of the electrosurgical generator by keying from terminals thereon is a step. The steps of connecting the terminals and the accessory and changing the rate controller in the accessory by adjusting the condition of its function per unit time in accord with the keying of the electrosurgical generator sensitive to the signal are preferably in the method.

The method may include the step of having a smoke evacuator or insufflator as the accessory and drawing fluid through a passage near the electrosurgical handpiece active electrode with the smoke evacuator. The additional step, of changing the smoke evacuator or insufflation from a low level of fluid flow through the passage from the active electrode to a high flow for drawing fluid from the area about the active electrode is made with the rate controller, might preferably be followed. Adjusting the rate controller so that the low level of fluid flow is that required for barely purging fluid through the passage from the active electrode and the high flow rate is for removing fluid in the vicinity of the active electrode a further preferred step.

The method may include the step providing signals from the terminals on the electrosurgical generator and deriving the signal from the trigger in response to instructions from the controller. The step of locating the switch on the handpiece for the keying of the electrosurgical generator is a preferred alternative. Another step locates the switch on the foot pedal for the keying of the electrosurgical generator.

The system for changing the rate of operation of an accessory used with an electrosurgical generator during treatment of a patient electrosurgically at an operative site may alternatively include a smoke detector associated with the electrode for determining when there is smoke thereabout. A smoke evacuator is preferably in the accessory and is most preferably plumbed to remove fluid from the area about the electrode at a low flow rate sufficient to move the fluid passed the smoke detector. The smoke detector delivers a signal indicative of smoke sensed thereby during operation of the electrosurgical generator. A rate controller in the smoke evacuator will adjust the condition of its function per unit time in accord with the operation of the electrosurgical generator because of the detected smoke.

DETAILED DESCRIPTION OF THE DRAWINGS

Figure 1:
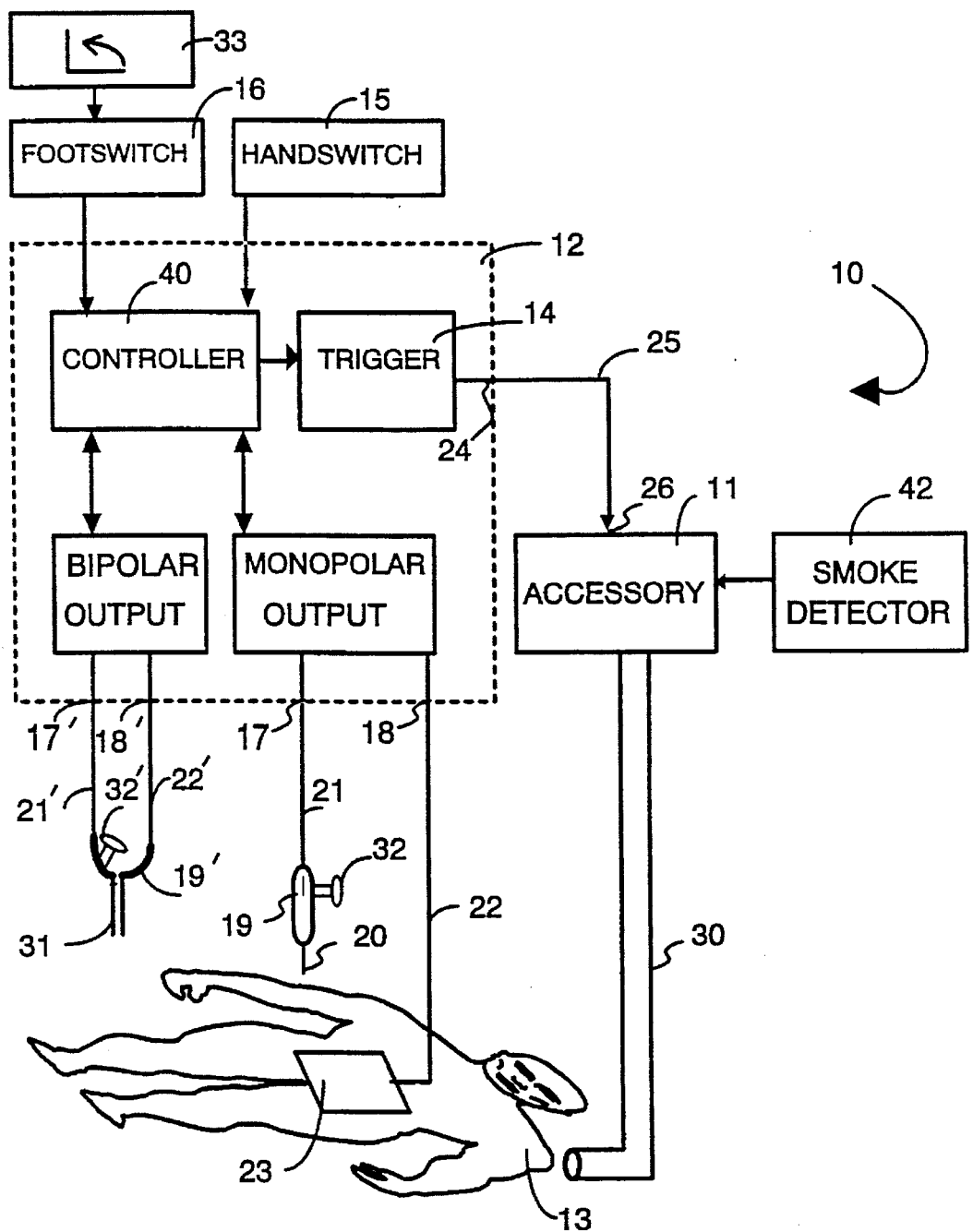
FIG. 1 is a schematic view showing an electrosurgical generator for use with a system for controlling the rate of an accessory such as a smoke evacuator or insufflator.

A system for changing the rate of operation 10 of an accessory 11 used with an electrosurgical generator 12 during treatment of a patient 13 electrosurgically at an operative site is schematically shown in FIG. 1. The accessory 11 and the electrosurgical generator 12 are connected to a source of energy such as a battery or mains to supply the basic power for operation. A trigger 14 for use in electrosurgery is disclosed schematically in FIGS. 1 and 2 and the trigger 14 is electrically connected with the electrosurgical generator 12 and the patient 13. A switch 15 or 16 connects in a conventional manner to activate the electrosurgical generator 12 when it is keyed during treatment of the patient 13. An active output 17 is electrically connected to the electrosurgical generator 12 for supplying radio frequency energy to the patient 13. A return input 18 is electrically connected to the electrosurgical generator 12 for receiving electrosurgical energy from the patient 13.

A monopolar electrosurgical handpiece 19 has at least an active electrode 20 carried thereby for use in providing electrosurgical procedures. A typical handpiece is Valleylab, Boulder, Colo. electrosurgical pencil model number 2502. An active lead 21 connects between the active output 17 and the electrosurgical handpiece active electrode 20. A return lead 22 connected to the return input 18 has a return pad 23 positioned relative to the patient 13 for completing the connection with the active electrode 20 so that RF energy passing therethrough may be returned to the electrosurgical generator 12 through the return input 18. One or more terminals 24, in FIGS. 1 and 2, on the electrosurgical generator 12 deliver one or more signals indicative of the use of the monopolar handpiece 19 to key the electrosurgical generator 12. One or more terminals 26 on the accessory 11 receives one or more signals through connections 25, as in FIGS. 1 and 3. The accessory 11 operates at a different rate when the electrosurgical generator 12 is keyed. Specifically, in FIG. 1 one or more connections 25, shown schematically as a cable, are between the terminals 24 and the accessory 11, which has one or more terminals 26 as shown in FIG. 3.

Figure 3:
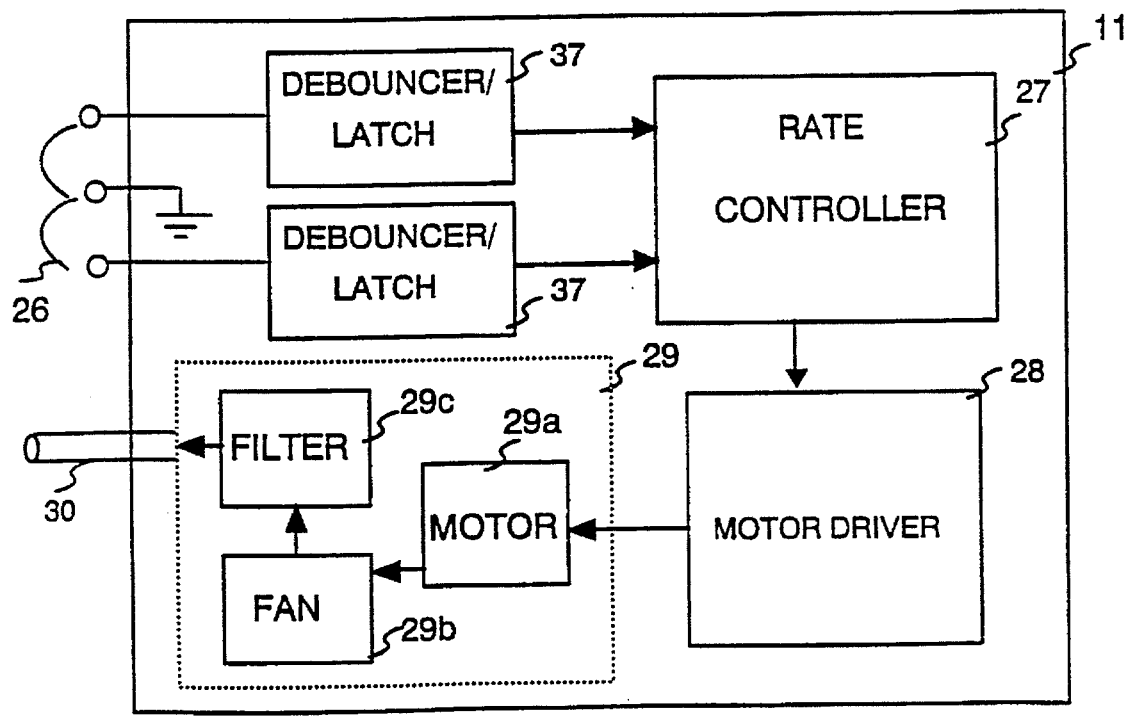
FIG. 3 is a schematic view of the circuitry in the accessory such as a smoke evacuator having a motor that is run at a different rates when the signals from the electrosurgical generator is received.

A rate controller 27 in the accessory 11 in FIG. 3 adjusts the condition of its function per unit time in accord with information from the trigger 14 in the electrosurgical generator 12. The rate controller 27 may contain a microprocessor such as the Motorolla 68HC811E to control its various functions. It may also contain a triac controller such as the Motorolla TDA 1185. A driver 28 in the accessory 11 includes a triac driver and triacs to provide timed current pulses at the correct phase angle to a smoke evacuator 29.

The smoke evacuator 29 of FIG. 3 may have a motor 29a, a fan 29b and a filter 29c, e.g. Air Force by Valleylab, Boulder, Colo. The smoke evacuator 29 is for drawing fluid such as electrosurgical debris and smoke particulates from a surgical site on patient 13 through a passage 30 near the electrosurgical handpiece active electrode 20 as schematically shown in FIG. 1. The passage 30 maybe associated with the handpiece 19 or included therein or thereon as disclosed for example in U.S. Pat. No. 4,562,838 which is incorporated as part of this disclosure. The rate controller 27 changes the smoke evacuator 29 from a low level of fluid flow through the passage 30 from about the active electrode 20 to a high flow for drawing fluid from the area about the active electrode 20. The rate controller 27, shown in FIG. 3, is adjustable so that the low level of fluid flow can be that required to barely purge fluid through the passage 30 from the active electrode 20 and the high flow rate is able to remove fluid in the vicinity of the active electrode 20.

Monopolar operation uses the return pad 23 connected to the patient 13 with the return lead 22. The return electrode 23 is preferably adhesively and conductively attached to the patient 13 and connects to the return lead 22 for electrosurgical effects between the active and return electrodes 20 and 23, respectively. Bipolar operation, also schematically shown in FIG. 1, includes leads 21' and 22' connected to the electrosurgical generator 12 carried on handpiece 19'. Bipolar electrodes 31 are carried thereon to permit electrosurgical effects when the electrosurgical generator 12 is keyed. While the passage 30 in FIG. 1 is shown schematically as ending near the patient 13, in either monopolar or bipolar operation the concept is to draw fluid away from the surgical site as quickly as it is generated during surgery. The leads 20' and 21' connect between the electrodes 31 of the bipolar handpiece 19' and terminals 17' and 18' on the electrosurgical generator 12. Terminals 17' and 18' are supplied with radio frequency electrosurgical energy for bipolar use and that is typically less than the energy available through the monopolar terminals 17 and 18. The monopolar and bipolar electrosurgical circuits, as shown in FIG. 1, are used alternatively and as used in the claims the electrosurgical circuit includes the path of the energy whether monopolar or bipolar. The electrosurgical circuit includes the electrosurgical generator output, the active lead, the active electrode, the patient's tissue, the return, the return lead and the electrosurgical generator input.

The terminals 17 or 17' and 18 or 18' of the electrosurgical generator 12 are triggered by foot switch 16 or hand switch 15, terminals 17 or 17' and 18 or 18' are connected physically inside the electrosurgical generator 12; the signals for foot switch 16 or hand switch 15 are remote as for example from the handpiece 19 or 19'. A handpiece switch 32 or 32' is located on the handpiece 19 or 19', respectively for the keying of the electrosurgical generator 12. A pedal switch 33 is similarly located remotely for foot operation and connects to the electrosurgical generator 12 for the keying as shown in FIG. 1 the pedal switch 33 or handpiece switch 32 or 32' can be alternatively used.

The accessory 11 could include a video monitor connected to the terminals 24 for receiving the signal to provide image or audio blanking during electrosurgery so as to reduce high frequency interference. The accessory 11 can include a light for the operative site and the rate controller 27 could also vary the light intensity by changing the intensity from a low level using minimal power to a high level for optimum observation and illumination. Similarly, the audio volume could be lowered or raised.

A method for changing the rate of operation of the accessory 11 used with the electrosurgical generator 12 during treatment of the patient 13 electrosurgically at an operative site includes steps. Providing the electrosurgical circuit between the electrosurgery, connects the electrosurgical generator 12 and the patient 13. Activating the electrosurgical generator 12 by keying the hand switch 15 or foot switch 16 with the trigger 14 during treatment of the patient 13. Performing electrosurgical procedures with the electrosurgical handpiece 19 or 19' in the electrosurgical circuit.

Operating the accessory 11 at a different rate when the electrosurgical generator 12 is keyed is a step of the method. Adjusting the function per unit time of the accessory 11 in accord with the keying of the electrosurgical generator 12 with the rate controller 27 is a step. Delivering signals indicative of the use of the electrosurgical generator 12 by keying, from terminals 24 thereon is another step. Connecting the terminals 24 and the accessory 11 and changing the rate controller 27 in the accessory 11 by adjusting the condition of its function per unit time in accord with the trigger 14 in the electrosurgical generator 12.

The method can have the steps of having the smoke evacuator 29 as the accessory 11 and drawing fluid through the passage 30 near the electrosurgical handpiece active electrodes 20 or 31 with the smoke evacuator 29. The method could include the step of changing the smoke evacuator 29 from a low level of fluid flow through the passage 30 from the active electrode 20 to a high fluid flow for drawing fluid from the area about the active electrode 20 is made with the rate controller 27. The method step of adjusting the rate controller 27 between the low level of fluid flow required for barely purging fluid through the passage 30 from the electrodes 20 or 31 and the high flow rate to remove fluid in the vicinity of the electrodes 20 or 31 and the reverse thereof is performed.

The method steps of providing signals from the terminals 24 on the electrosurgical generator 12 and deriving those signals from the output 17 or 17' when the electrosurgical generator 12 is keyed are performed. The method step locates the hand switch 15 on the handpiece 19 or 19' to key the electrosurgical generator 12. The method step operates the foot switch 16 with the foot pedal 33 to key the electrosurgical generator 12.

The system 10 changes the rate of operation in accord with a smoke detector 42 used with the electrosurgical generator 12 during treatment of the patient 13 electrosurgically at an operative site. The smoke detector 42 responsive to the active electrodes 20 or 31 determines when there is smoke thereabout. The smoke detector 42 may be physically located in the passage 30. The smoke detector 42 delivers signals indicative of smoke sensed thereby during operation of the electrosurgical generator 12 and so signals the smoke evacuator 29 when the electrosurgical generator 12 is keyed. The smoke evacuator 29 is plumbed to remove fluid from the area about the active electrodes 20 or 31 at a low flow rate sufficient to move the fluid passed the smoke detector 34 and to keep the passage 30 with a slight negative pressure. The passage 30 may be located in the handpiece 19.

In a preferred configuration, the electrosurgical generator 12 is made by Valleylab, Boulder, Colo., and designated SSE3B. The connections 26 are electrically coupled to debouncer and latching circuits 37 that assure that only one switch pulse is supplied to the rate controller 27. The rate controller preferably consists of a microcontroller such as a 68HC811E made by Motorola of Phoenix, Ariz., and a triac controller such as TDA 1185 arranged to supply signals to the motor driver 28. The motor driver 28 includes a triac motor driver and triacs to provide timed current pulses at the correct phase angle to the smoke evacuator 29. In particular, the sine wave form is on a portion of the cycle in accord with the rate controller 27 instructions and the driver 28 input to the smoke evacuator 29 in the form of high speed electric motor 29a driving fan 29b to draw fluid through passage 30 and then past filter 29c and, if desired, a fluid trap before smoke particulates and fluid can reach the atmosphere.

Figure 2:
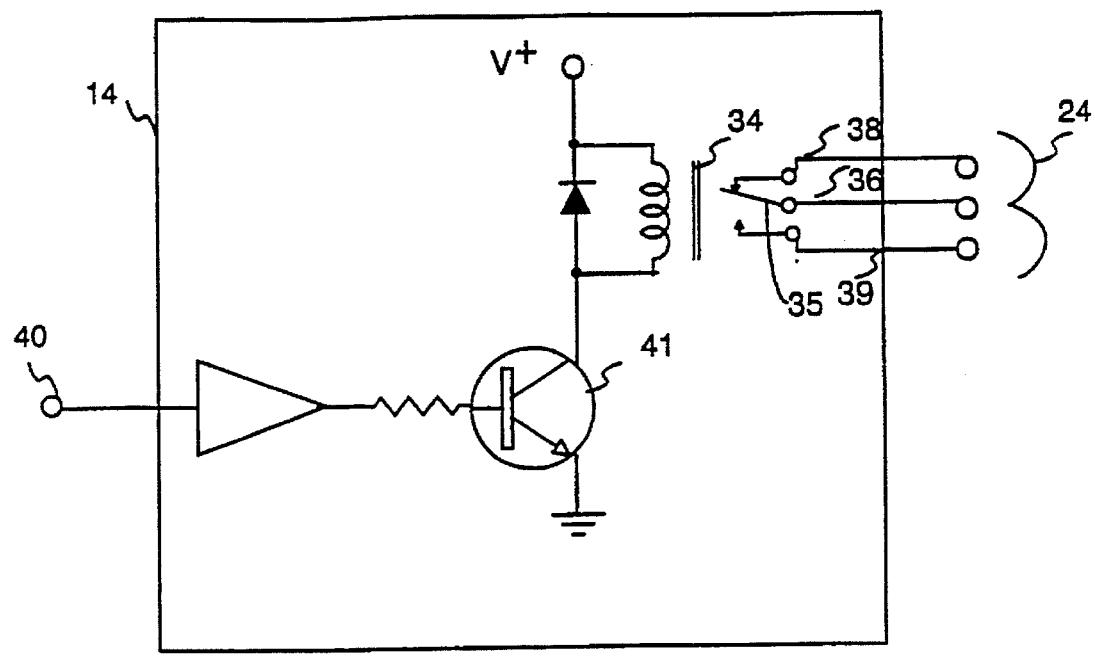
FIG. 2 is a schematic view of the circuitry in the electrosurgical generator that signals the accessory when the electrosurgical generator of FIG. 1 has been keyed.

The connections 24 on trigger 14 provide signals in accordance to the operation of a relay 34, shown in FIG. 2 wherein the relay 34 pulls a movable contact 35 from its normally closed position against a center contact lead 36 and makes a connection with an upper lead 38. When the electrosurgical generator 12 is keyed, a controller 40 in the electrosurgical generator 12 sends current to a transistor 41 in the trigger 14 and thus provides power to activate and hold relay 34. After release of the keyed electrosurgical generator 12, the activated and held relay 34 is deenergized and movable contact 35 moves to close against center lead 36 and thus a lower lead 39 is connected. The connection of center lead 36 and lower lead 39 sends a signal to the accessory 11 and more particularly through debouncer and latching circuit 37.

While a particular circuit has been disclosed, the invention sought to be protected in the claims that follow includes systems and techniques that change the rate of the operation of the accessory upon the activation of the electrosurgical generator.

What is claimed is:

1. A system for operating a smoke evacuator at either a high or low flow rate when used with an electrosurgical generator during treatment of a patient, the electrosurgical generator having at least one active electrode, the smoke evacuator having a passage for carrying smoke away from the at least one active electrode, the system comprising:

an electrosurgical circuit for use during electrosurgery, the electrosurgical circuit located and connected between the electrosurgical generator and the patient for transmission of electrosurgical energy therebetween;

a switch connected to the electrosurgical circuit, the switch for activating the electrosurgical generator when the switch is closed during treatment of the patient;

an output on the electrosurgical generator for sending an electrical signal when the switch is closed;

a smoke evacuator connected to receive the electrical signal from the output, the smoke evacuator to operate at high or low flow rates in response to the signal;

a low level of fluid flow rate controller connected to the smoke evacuator for the operation for the smoke evacuator, the low level of fluid flow rate controller set to barely purge fluid through the passage from the active electrode, the low level of fluid flow rate controller to slowly move fluid through the passage;

a high flow rate controller connected to the smoke evacuator for the operation of the smoke evacuator, the high flow rate controller for operating the smoke evacuator to remove fluid from the vicinity of the at least one active electrode, and wherein the smoke evacuator changes from the low level of fluid flow rate to the high flow rate whenever the electrical signal is received and from the high flow rate to the low level fluid flow rate whenever the signal is absent.

2. The system of claim 1 wherein the rate controller is adjustable so that the low level of fluid flow rate is that required to barely purge fluid through the passage from the operative site and the high flow rate is able to remove fluid in the vicinity of the operative site.

3. The system of claim 1 wherein there are terminals on the electrosurgical generator electrically coupled to a trigger therein to provide the signal when the switch of the electrosurgical generator is closed, the trigger electrically coupled and responsive to closing of the switch, the trigger for signaling the need for a change in the rate of operation during treatment of the patient.

4. The system of claim 1 wherein the smoke evacuator includes a fan connected to a driver in the smoke evacuator connects to the rate controller for changing the operation of the smoke evacuator in accord with the rate controller by adjusting the condition of the smoke evacuator function per unit time in accord with the switching of the electrosurgical generator.

5. The system of claim 4 wherein the smoke evacuator includes a filter to trap particulates in the smoke during electrosurgery.

6. The system of claim 1 wherein the switch is located on the handpiece, the switch is connected to the electrosurgical generator for operating of the electrosurgical generator.

7. The system of claim 1 wherein the switch has a pedal on a footswitch for foot operation and the switch connects to the electrosurgical generator for operating the electrosurgical generator.

8. The system of claim 4 wherein a smoke detector is contained in the passage for sensing smoke therein.

9. The system of claim 8 wherein the passage is located near the handpiece to draw in smoke from the operative site.

10. A method for changing the rate of operation between a high or low flow rate for a smoke evacuator used with an electrosurgical generator during treatment of a patient electrosurgically at an operative site, having the steps of:

having an electrosurgical circuit for electrosurgery, the electrosurgical circuit located and connected between the electrosurgical generator and the patient for transmission of electrosurgical energy therebetween;

connecting a switch in the electrosurgical circuit to activate the electrosurgical generator when closing the switch during treatment of the patient;

supplying radio frequency energy for the patient to an active output in the electrosurgical circuit and electrically connecting the active output to the electrosurgical generator;

returning electrosurgical energy through the electrosurgical circuit from the patient and into a return input in the electrosurgical circuit, electrically connecting the return input to the electrosurgical generator;

providing an electrosurgical handpiece in the electrosurgical circuit and the electrosurgical handpiece having at least an active electrode carried thereby for use in performing electrosurgical procedures;

connecting active and return leads in the electrosurgical circuit between the respective active output, active electrode, return input and patient return;

having a return positioned relative to the patient for completing the electrosurgical circuit with the active electrode for returning RF energy passing therethrough to the electrosurgical generator through the return lead to the return input;

operating the smoke evacuator at a different rate when the electrosurgical generator switch is keyed;

adjusting the smoke evacuator for the condition of its function per unit time in accord with the keying of the electrosurgical generator switch with a rate controller;

connecting with a cable between terminals on the electrosurgical generator and the accessory, and delivering signals of switch closing from terminals with a trigger, the signals delivered to the accessory and signals indicative of the use of the electrosurgical generator;

changing the rate controller in the accessory by adjusting the condition of its function per unit time in accord with the switch closing for the electrosurgical generator, and driving the accessory with a driver connected to the rate controller.

11. The method of claim 10 with the step of drawing fluid through a passage near an electrosurgical handpiece and the operative site with the smoke evacuator.

12. The method of claim 10 with the step of changing the rate of speed of the smoke evacuator from a low level of fluid flow through the passage from the operative site to a high flow for drawing fluid from the area about the operative site is made with the rate controller.

13. The method of claim 12 with the step of adjusting the rate controller so that the low level of fluid flow is that which may be required for barely purging fluid through the passage from the operative site and the high flow rate is for removing fluid in the vicinity of the operative site.

14. The method of claim 10 with the step of triggering to provide signals from the terminals on the electrosurgical generator based upon deriving the signals from a smoke detector associated with the passage.

15. The method of claim 11 with the step of operating the electrosurgical generator with the switch located on the electrosurgical handpiece.

16. The method of claim 10 with the step of operating the electrosurgical generator with the switch located on a foot pedal.

17. A system for changing the rate of operation of a smoke evacuator used with an electrosurgical generator during treatment of a patient electrosurgically at an operative site, the system comprising:

an electrosurgical circuit for use in electrosurgery, the electrosurgical circuit located and connected between the electrosurgical generator and the patient;

a switch in the electrosurgical circuit, the switch connected to activate the electrosurgical generator when closed during treatment of the patient;

an active output in the electrosurgical circuit, the active output electrically connected to the electrosurgical generator for supplying radio frequency energy to the electrosurgical circuit for delivery through the patient;

a return input in the electrosurgical circuit, the return input electrically connected to the electrosurgical generator for receiving electrosurgical energy in the electrosurgical circuit passing through the patient;

an electrosurgical handpiece in the electrosurgical circuit, the electrosurgical handpiece having at least an active electrode carried thereby for use in providing electrosurgical procedures;

an active lead connected in the electrosurgical circuit between the active output and the electrosurgical handpiece active electrode;

a return lead connected in the electrosurgical circuit to the return input, the return lead having a return positioned relative to the patient for completing the electrosurgical circuit with the active electrode so that RF energy passing therethrough may be returned to the electrosurgical generator through the return input;

a smoke detector responsive to smoke generated at the operative site, the smoke detector for determining when there is smoke thereabout, the smoke detector for signaling smoke thereabout during operation of the electrosurgical generator;

a smoke evacuator connected to the electrosurgical generator, the smoke evacuator for operating at either a high or low flow rate when the electrosurgical generator switch is closed, the smoke evacuator plumbed to remove fluid from the area about the active electrode near the operative site at a low flow rate sufficient to move the fluid passed the smoke detector;

a rate controller in the smoke evacuator for operation of the smoke evacuator at a high flow per unit time in accord with the operation of the electrosurgical generator, the rate controller connected to receive signals from the smoke evacuator;

a driver in the smoke evacuator connected to the rate controller and the smoke evacuator, the driver for changing the smoke evacuator by adjusting the rate of its operation per unit time in accord with the rate controller signal of the smoke detected and wherein the smoke evacuator changes from the low level of fluid flow rate to the high flow rate whenever the electrical signal is received and from the high flow rate to the low level fluid flow rate whenever the signal is absent.

\* \* \* \* \*